United States Patent [19]

Englert et al.

[11] Patent Number: 5,364,868
[45] Date of Patent: Nov. 15, 1994

[54] AMINO-SUBSTITUTED BENZOYLGUANIDINES, PROCESS FOR THEIR PREPARATION, THEIR USE AS A MEDICAMENT AND MEDICAMENT CONTAINING THEM

[75] Inventors: Heinrich Englert, Hofheim am Taunus; Dieter Mania, Königstein/Taunus; Hans-Jochen Lang, Hofheim am Taunus; Wolfgang Scholz, Eschborn; Wolfgang Linz, Mainz; Udo Albus, Florstadt, all of Germany

[73] Assignee: Hoechst Aktiengesellschaft, Frankfurt am Main, Germany

[21] Appl. No.: 16,535

[22] Filed: Feb. 11, 1993

[30] Foreign Application Priority Data

Feb. 15, 1992 [DE] Germany .............................. 4204577

[51] Int. Cl.⁵ .................. A61K 31/445; C07D 211/28; C07D 207/06; C07C 279/10
[52] U.S. Cl. ..................... 514/331; 514/429; 514/183; 514/212; 514/218; 514/222.2; 514/226.8; 514/227.5; 514/228.8; 514/247; 514/255; 514/256; 514/634; 514/637; 540/450; 540/470; 540/484; 540/544; 540/553; 540/575; 546/231; 544/3; 544/53; 544/59; 544/63; 544/88; 544/169; 544/224; 544/238; 544/373; 548/567; 548/577; 564/237
[58] Field of Search ............... 546/231; 548/567, 577; 564/237; 540/450, 470, 484, 544, 553, 575; 544/3, 53, 59, 63, 88, 169, 224, 238, 373; 514/183, 212, 218, 222.2, 226.8, 227.5, 228.8, 247, 255, 256, 331, 429, 634, 637

[56] References Cited

U.S. PATENT DOCUMENTS

| | | | |
|---|---|---|---|
| 3,006,913 | 10/1961 | Mull | 540/450 |
| 3,780,027 | 12/1973 | Cragoe, Jr. et al. | 549/494 |
| 3,968,243 | 7/1976 | Maxwell | 514/634 |
| 4,318,915 | 3/1982 | Cohnen | 514/634 |
| 4,602,041 | 7/1986 | Newsome | 564/237 |
| 5,006,523 | 4/1991 | Atwal | 514/634 |
| 5,091,394 | 2/1992 | Englert | 564/237 |
| 5,190,976 | 3/1993 | Weber | 514/634 |

FOREIGN PATENT DOCUMENTS 0416499 3/1991 European Pat. Off. .

OTHER PUBLICATIONS

Caton "Benzamido–Derivatives of Et-2-NH-2-4-Me-Pyrimidine-5-Carboxylate" J. Chem. Soc. (C) 1269–70 (1969).

Riesz et al "Chemical Composition and Affinity for Macromolecular Compound" Chem. Abs. 62 1763g (1965).

W. Scholz, et al. "Effects of Na+/H+ Exchange Inhibitors in Cardiac Ischemia," J. Mol. Cell Cardiol. 24, 731–740 (1992).

E. Riesz, et al. "Constitution chimique et affinite pour les composes macromoleculaires. I. Recherches sur les derives benzoyles de la quanidine" Bulletin de la Societe chimique de France, 1964, pp. 1517–1524.

*Primary Examiner*—Celia Chang
*Attorney, Agent, or Firm*—Finnegan, Henderson, Farabow, Garrett & Dunner

[57] ABSTRACT

Amino-substituted benzoylguanidines, process for their preparation, their use as a medicament and medicament containing them Benzoylguanidines of the formula I

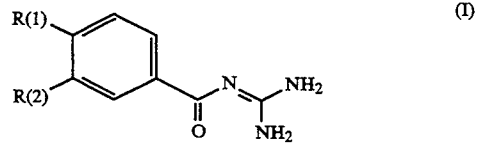

are described in which R(1) or R(2) is an amino group —NR(3)R(4), where R(3) and R(4) are H or (cyclo)alkyl or R(3) is phenyl-$(CH_2)_p$— where p=0, 1, 2, 3 or 4, or phenyl, or R(3) and R(4) can also together be a methylene chain, and in which the other substituent R(1) or R(2) in each case is H, F, Cl, alkyl, alkoxy, $CF_3$, $C_mF_{2m+1}$—$CH_2$—, benzyl or phenoxy, and their pharmaceutically tolerable salts.

(Abstract continued on next page.)

The compounds according to the invention have very good antiarrhythmic properties, as occur, for example, in the case of oxygen deficiency symptoms. The compounds are used as antiarrhythmic pharmaceuticals having a cardioprotective component for infarct prophylaxis and infarct treatment as well as for the treatment of angina pectoris, where they also preventively inhibit or greatly decrease the pathophysiological processes in the formation of ischemically induced damage, in particular in the production of ischemically induced cardiac arrhythmias.

7 Claims, No Drawings

AMINO-SUBSTITUTED BENZOYLGUANIDINES, PROCESS FOR THEIR PREPARATION, THEIR USE AS A MEDICAMENT AND MEDICAMENT CONTAINING THEM

The invention relates to benzoylguanidines of the formula I

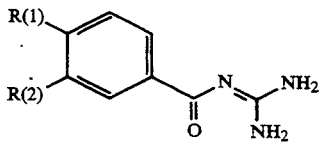

in which:

R(1) or R(2) is an amino group —NR(3)R(4), where R(3) and R(4)—identical or different—are H, $C_1$-$C_6$-alkyl or $C_3$-$C_7$-cycloalkyl, or R(3) is phenyl-(CH$_2$)$_p$- where p is 0, 1, 2, 3 or 4, or phenyl, where phenyl in each case is unsubstituted or carries one or two substituents from the groups fluorine, chlorine, methyl or methoxy, R(3) and R(4) can also together be a straight-chain or branched $C_4$-$C_7$-methylene chain, where a —CH$_2$— member of the methylene chain can be replaced by oxygen, S or NR(5) and R(5) is H or lower alkyl, the other substituent R(1) or R(2) in each case is H, F, Cl, $C_1$-$C_4$-alkyl, $C_1$-$C_4$-alkoxy, $CF_3$, $C_mF_{2m+1}$—CH$_2$—, benzyl or phenoxy, where the respective phenyl radical is unsubstituted or carries one to two substituents having the meaning methyl, methoxy, fluorine or chlorine, and in which m is 1, 2 or 3, and their pharmaceutically tolerable salts.

If one of the substituents R(1) to R(4) contains a center of asymmetry, the invention includes compounds having both the S and R configurations. The compounds can be present as optical isomers, as diastereoisomers, as racemates or as mixtures thereof.

The designated alkyl radicals can be present either in straight-chain or branched form.

Preferred compounds of the formula I are those in which: one of the two substituents R(1) or R(2) is an amino group —NR(3)R(4)
in which R(3) and R(4) together are a methylene chain (CH$_2$)$_n$ where n=4-5
and the other respective substituent R(1) or R(2) is chlorine or phenoxy.

Particularly preferred compounds are 4-chloro-3-(1-pyrrolidino)benzoylguanidine, 4-methyl-3-(1-pyrrolidino)benzoylguanidine, 4-chloro-3-(1-piperidino)-benzoylguanidine, 4-methyl-3-(1-piperidino)benzoylguanidine, 4-phenoxy-3-(1-pyrrolidino)benzoylguanidine and 4-(2-chlorophenoxy)-3-(1-pyrrolidino)benzoylguanidine and their pharmacologically tolerable salts.

The compounds I are substituted acylguanidines.

A prominent ester representative of the acylguanidines is the pyrazine derivative amiloride, which is used in therapy as a potassium-sparing diuretic. Numerous other compounds of the amiloride type are described in the literature, such as, for example, dimethylamiloride or ethylisopropylamiloride.

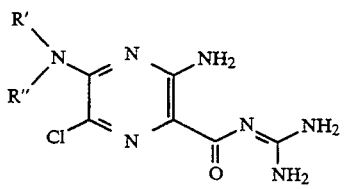

Amiloride: R', R''=H
Dimethylamiloride: R', R''=CH$_3$
Ethylisopropylamiloride: R'=C$_2$H$_5$, R''=CH(CH$_3$)$_2$ Investigations have moreover been disclosed which point to antiarrhythmic properties of amiloride (Circulation 79, 1257-63 (1989)). Obstacles to wide use as an antiarrhythmic are, however, that this effect is only slightly pronounced and occurs accompanied by a hypotensive and salutetic action and these side effects are undesired in the treatment of cardiac arrhythmias.

Indications of antiarrhythmic properties of amiloride were also obtained in experiments on isolated animal hearts (Eur. Heart J. 9 (suppl.1): 167 (1988) (book of abstracts)). For instance, it was found in rat hearts that an artificially induced ventricular fibrillation could be suppressed completely by amiloride. The abovementioned amiloride derivative ethylisopropylamiloride was even more potent than amiloride in this model.

In U.S. Pat. 3,780,027, acylguanidines are claimed which are structurally similar to the compounds of the formula I. The crucial difference to the compounds I according to the invention is that they are trisubstituted benzoylguanidines which in their substitution pattern are derived from commercially available diuretics, such as bumetanide and furosemide, and carry an important amino group for the desired salidiuretic action in position 2 or 3 relative to the carbonylguanidine group. A strong salidiuretic activity is correspondingly reported for these compounds.

In EP 91416499 (HOE 89/F 288), benzoylguanidines are claimed which carry SO$_n$ radicals in the position corresponding to the radical R(2). They have only antiarrhythmic actions.

It was therefore surprising that the compounds according to the invention have no undesired and disadvantageous salidiuretic properties, but very good antiarrhythmic properties, as occur, for example, in the case of oxygen deficiency symptoms. As a result of their pharmacological properties, the compounds are outstandingly suitable as antiarrhythmic pharmaceuticals having a cardioprotective component for infarct prophylaxis and infarct treatment and for the treatment of angina pectoris, where they also preventively inhibit or greatly decrease the pathophysiological processes in the formation of ischemically induced damage, in particular in the production of ischemically induced cardiac arrhythmias. Because of their protective actions against pathological hypoxic and ischemic situations, the compounds of the formula I according to the invention can be used as a result of inhibition of the cellular Na$^+$/H$^+$ exchange mechanism as pharmaceuticals for the treatment of all acute or chronic damage caused by ischemia or primary or secondary diseases induced thereby. This relates to their use as pharmaceuticals for surgical interventions, for example in organ transplantation, where the compounds can be used both for the protection of the organs in the donor before and during removal, for the protection of removed organs, for example during treatment with or storage thereof in physiological bath fluids, and during transfer to the body of the recipient. The compounds are also useful, protective pharmaceuticals during the performance of angioplastic surgical interventions, for example in the heart and in peripheral vessels. In accordance with their protective action against ischemically induced damage, the compounds are also suitable as pharmaceuticals for the treatment of ischemias of the nervous system, in particular the central nervous system, where they are suitable, for example, for the treatment of strokes or of cerebral oedema. Moreover, the compounds of the formula I according to the invention are also suitable for the treatment of forms of shock, such as, for example, allergic, cardiogenic, hypovolemic and bacterial shock.

Moreover, the compounds of the formula I according to the invention are distinguished by potent inhibitory action on the proliferation of cells, for example fibroblast cell proliferation and the proliferation of vascular smooth muscle cells. The compounds of the formula I can therefore be considered as useful therapeutics for diseases in which cell proliferation is a primary or secondary cause, and can therefore be used as anti-atherosclerotics, agents against late-onset diabetic complications, cancers, fibrotic diseases such as pulmonary fibrosis, fibrosis of the liver or fibrosis of the kidneys, organ hypertrophy and hyperplasia, in particular in prostate hyperplasia or prostate hypertrophy.

The compounds according to the invention are active inhibitors of the cellular sodium-proton antiporter ($Na^+/H^+$ exchanger), which is raised in numerous diseases (essential hypertension, atherosclerosis, diabetes, etc.) even in those cells which are easily accessible to measurements, such as, for example, in erythrocytes, thrombocytes or leucocytes. The compounds according to the invention are therefore suitable as excellent and simple scientific tools, for example in their use as diagnostics for the determination and differentiation of certain forms of hypertension, but also of atherosclerosis or of diabetes, proliferative diseases, etc. Moreover, the compounds of the formula I are suitable for preventive therapy for the prevention of the formation of high blood pressure, for example of essential hypertension.

The invention furthermore relates to a process for the preparation of the compounds I, which comprises reacting compounds of the formula II

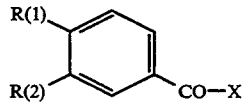

(II)

with guanidine of the formula III

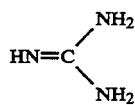

(III)

in which R(1) and R(2) have the given meaning and X is a leaving group which can be easily nucleophilically substituted.

The activated acid derivatives of the formula II in which X is an alkoxy group, preferably a methoxy group, a phenoxy group, or phenylthio, methylthio or 2-pyridylthio group, or a nitrogen heterocycle, preferably 1-imidazolyl, are advantageously obtained in a manner known per se from the carbonyl chlorides (formula II, X=Cl) on which they are based, which for their part can in turn be prepared in a manner known per se from the carboxylic acids (formula II, X=OH) on which they are based, for example using thionyl chloride.

In addition to the carbonyl chlorides of the formula II (X=Cl), other activated acid derivatives of the formula II can also be prepared in a manner known per se directly from the benzoic acid derivatives (formula II, X=OH) on which they are based, such as, for example, the methyl esters of the formula II where X=OCH$_3$ by treatment with gaseous HCl in methanol, the imidazolides of the formula II by treatment with carbonyldiimidazole (X=1-imidazolyl, Staab, Angew. Chem. Int. Ed. Engl. 1, 351-367 (1962)), the mixed anhydrides II using Cl—COOC$_2$H$_5$ or tosyl chloride in the presence of triethylamine in an inert solvent, and also the activation of benzoic acids using dicyclohexylcarbodiimide (DCC). A number of suitable methods for the preparation of activated carboxylic acid derivatives of the formula II are given under details of source literature in J. March, Advanced Organic Chemistry, Third Edition (John Wiley & Sons, 1985), p. 350.

The reaction of an activated carboxylic acid derivative of the formula I with guanidine of the formula III is carried out in a manner known per se in a protic or aprotic polar but inert organic solvent. These solvents have proven suitable in the reaction of the methylbenzoates (II, X=OMe) with guanidine in methanol or THF between 20° C. and the boiling point. In most reactions of compounds II with guanidines III as free bases, the reaction was advantageously carried out in aprotic inert solvents such as THF, dimethoxyethane or dioxane. However, water can also be used as a solvent in the reaction of II and III.

If X is chlorine, the reaction is advantageously carried out with the addition of an acid scavenger, for example in the form of excess guanidine for binding the hydrohalic acid.

Some of the underlying benzoic acid derivatives of the formula II and the guanidine used of the formula III are known and described in the literature. The unknown compounds of the formula II can be prepared by methods known from the literature by converting, for example, a methyl benzoate II where R(1) and R(2) have the meaning mentioned at the beginning, specifically where R(3) and R(4) are H, and X is, for example, OCH$_3$, using a dicarboxylic anhydride such as, for example, glutaric anhydride or succinic anhydride into a compound of the formula IV in which R(1) or R(2) is now a cyclic imide of the formula IVa where n in the methylene chain is 3 to 7.

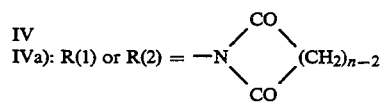

IV
IVa): R(1) or R(2) =

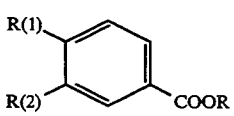

IVb): R(1) or R(2) =

This imide IVa is then converted by the action of sodium borohydride and boron trifluoride etherate into the corresponding methyl benzoate of the formula IVb. This can be further reacted directly with guanidine to give compounds of the formula I.

In general, benzoylguanidines I are weak bases and can bind acid with the formation of salts. Possible acid addition salts are salts of all pharmacologically tolerable acids, for example halides, in particular hydrochlorides, lactates, sulfates, citrates, tartrates, acetates, phosphates, methanesulfonates and p-toluenesulfonates.

Pharmaceuticals which contain a compound I can be administered orally, parenterally, intravenously, rectally or by inhalation, the preferred administration being dependent on the particular course of the disease. The compounds I can be used on their own or together with pharmaceutical auxiliaries, to be precise in veterinary and in human medicine.

The auxiliaries which are suitable for the desired pharmaceutical formulation are familiar to the person skilled in the art on the basis of his knowledge. In addition to solvents, gelling agents, suppository bases, tabletting auxiliaries and other active compound excipients, antioxidants, dispersants, emulsifiers, anti-foams, flavor correctants, preservatives, solubilizers or colorants, for example, can be used.

For a form for oral administration, the active compounds are mixed with the additives suitable for this purpose, such as excipients, stabilizers or inert diluents, and are brought by the customary methods into the suitable administration forms, such as tablets, coated tablets, hard gelatine capsules, or aqueous, alcoholic or oily solutions. Inert excipients which can be used are, for example, gum arabic, magnesia, magnesium carbonate, potassium phosphate, lactose, glucose or starch, in particular corn starch. Preparation can be carried out here both as dry and as moist granules. Suitable oily excipients or solvents are, for example, vegetable or animal oils, such as sunflower oil or fish liver oil.

For subcutaneous or intravenous administration, the active compounds are brought into solution, suspension or emulsion, if desired using the substances customary for this purpose such as solubilizers, emulsifiers or other auxiliaries. Suitable solvents are, for example: water, physiological saline solution or alcohols, for example ethanol, propanol, glycerol, and also sugar solutions such as glucose or mannitol solutions, or alternatively a mixture of the various solvents mentioned.

Pharmaceutical formulations suitable for administration in the form of aerosols or sprays are, for example, solutions, suspensions or emulsions of the active compound of the formula I in a pharmaceutically acceptable solvent, such as, in particular, ethanol or water, or a mixture of these solvents.

If required, the formulation can also contain still other pharmaceutical auxiliaries such as surfactants, emulsifiers and stabilizers as well as a propellant gas. Such a preparation contains the active compound customarily in a concentration from about 0.1 to 10, in particular from about 0.3 to 3% by weight.

The dose of the active compound of the formula I to be administered and the frequency of administration depend on the potency and duration of action of the compounds used and additionally on the type and severity of the disease to be treated and on the sex, age, weight and individual responsiveness of the mammal to be treated.

On average, the daily dose of a compound of the formula I in a patient of weight about 75 kg is at least 0.001 mg, preferably 0.01 mg to 10 mg, preferably 1 mg. In acute episodes of the disease, for example immediately after suffering a cardiac infarct, even higher and in particular more frequent dosages may be necessary, for example up to 4 individual doses per day. In particular when administered i.v., for example in the case of an infarct patient in the intensive care ward, up to 100 mg per day may be necessary.

EXPERIMENTAL SECTION

General reaction procedure (procedure A) for the reaction of the compounds of the formula II where X has the meaning $OCH_3$ to give benzoylguanidine hydrochlorides I.

Method A 0.02 mol of the methyl ester II are dissolved in 50 ml of methanol and treated under a protective gas atmosphere (argon) with 3.6 g of guanidine (free base). The mixture is heated under reflux for 12 h, the solvent is removed by evaporation in vacuo and the residue is taken up in water. Extraction with methylene chloride and evaporation of the solvent yield an oily residue which, after dissolving in methanolic HCl, is precipitated again by addition of ether. The oil thus obtained is purified by chromatography on silica gel (eluent: methylene chloride/methanol 20:1).

General procedure (procedure B) for the preparation of benzoylguanidines (I) from benzoic acids (II, X=OH)

0.01 mol of the benzoic acid derivative of the formula II (X=OH) is dissolved or suspended in 60 ml of anhydrous THF and then treated with 1.78 g (0.011 mol) of carbonyldiimidazole. After stirring for 2 hours at room temperature, 2.95 g (0.05 mol) of guanidine are introduced into the reaction solution. After stirring over night, the THF is distilled off under reduced pressure (Rotavapor), the residue is treated with water, the mixture is adjusted to pH 6–7 with 2N hydrochloric acid and the corresponding benzoylguanidine derivative (formula I) is filtered off.

The benzoylguanidines thus obtained can be converted into the corresponding salts by treatment with aqueous or methanolic hydrochloric acid or other pharmacologically tolerable acids.

The cyclic imide IVa (0.05 mol) is dissolved in 50 ml of diglyme and treated with 14.1 ml (0.1144 mol) of $BF_3 \cdot Et_2O$. After cooling to 0°–5° C., 4.3 g (0.1144 mol) of $NaBH_4$ are added at a maximum of 5° C. and the mixture is stirred at less than 5° C. for 6 h. It is then poured onto ice-$H_2O$ and the precipitated oil is separated off by decantation. Taking up in ethyl acetate, drying with $MgSO_4$ and evaporation of the solvent yields the desired product, which can in general be reacted without further purification to give the acylguanidine I.

General procedure for the preparation of cyclic imides IVa from amines IVb 0.1 mol of the amine of the formula IVb and 0.3 mol of a dicarboxylic acid anhydride such as, for example, succinic anhydride or glutaric anhydride are fused at 180° C. and heated at this temperature for 10 h. The mixture is then taken up in methanol and stirred into water. The product which crystallizes is filtered off with suction and recrystallized from ethanol.

EXAMPLE 1

4-Phenoxy-3-N-pyrrolidinobenzoylguanidine hydrochloride

From methyl 4-phenoxy-3-N-pyrrolidinobenzoate and guanidine. Melting point: 225°–227° C.; MS: M+ =324 (calc. mol. wt.=324.37), procedure A

EXAMPLE 2

4-Methyl-3-N-pyrrolidinobenzoylguanidine hydrochloride

From methyl 4-methyl-3-N-pyrrolidinobenzoylbenzoate and guanidine (procedure A). Melting point: 235°–238° C.; MS: M+ =226 (calc. mol. wt.=226.67)

EXAMPLE 3

4-Chloro-3-N-ethylaminobenzoylguanidine hydrochloride

From methyl 4-chloro-3-N-ethylaminobenzoate and guanidine (procedure A). Melting point: 196°–198° C.; MS: M+ =240 (calc. mol. wt.–240.69)

EXAMPLE 4

4-Phenoxy-3-N-propylaminoguanidine hydrochloride

From methyl 4-phenoxy-3-N-propylaminobenzoate and guanidine (procedure A). Melting point: 221°–223° C.; MS: M+ =312 (calc. mol. wt.=312.36)

EXAMPLE 5

4-Chloro-3-N-pyrrolidinobenzoylguanidine hydrochloride

From methyl 4-chloro-3-N-pyrrolidinobenzoate and guanidine (procedure A). Melting point: 268°–270° C.; MS: M+ =358 (calc. mol. wt.=266.73)

EXAMPLE 6

4-Methoxy-3-N-propylaminoguanidine hydrochloride

From methyl 4-methoxy-3-N-propylaminobenzoate and guanidine (procedure A). Melting point: 231°–233° C.; MS: M+ =250 (calc. mol. wt.=250.30)

EXAMPLE 7

4-Chloro-3-N-benzylaminoguanidine hydrochloride

From methyl 4-chloro-3-N-benzylaminobenzoate and guanidine (procedure A). Melting point: 91°–93° C.; MS: M+ =302 (calc. mol. wt.=302.76)

EXAMPLE 8

4-(2-Chlorophenoxy)-3-N-pyrrolidinobenzoylguanidine hydrochloride

From methyl 4-(2-chlorophenoxy)-3-N-pyrrolidinobenzoate and guanidine (procedure A). Melting point: 121° C.; MS: M+ =358 (calc. mol. wt.=358.82)

EXAMPLE 9

4-(2,3-Dichlorophenoxy)-3-N-pyrrolidinobenzoylguanidine hydrochloride

From methyl 4-(2,3-dichlorophenoxy)-3-N-pyrrolidinobenzoate and guanidine (procedure A). Melting point: 169°–170° C.; MS: M+ =391 (calc. mol. wt.=393.27)

EXAMPLE 10

4-(2-Methylphenoxy)-3-N-pyrrolidinobenzoylguanidine hydrochloride

From methyl 4-(2-methylphenoxy)-3-N-pyrrolidinobenzoate and guanidine (procedure A). Melting point: 185°–200° C.; MS: M+ =338 (calc. mol. wt.–338.4)

EXAMPLE 11

4-(4-Chlorophenoxy)-3-N-pyrrolidinobenzoylguanidine hydrochloride

From methyl 4-(4-chlorophenoxy)-3-N-pyrrolidinobenzoate and guanidine (procedure A). Melting point: 120°–135° C.; MS: M+ =358 (calc. mol. wt.=358.82)

EXAMPLE 12

4-(2-Methoxyphenoxy)-3-N-pyrrolidinobenzoylguanidine hydrochloride

From methyl 4-(2-methoxyphenoxy)-3-N-pyrrolidinobenzoate and guanidine (procedure A). Melting point: 180°–195° C.; MS: M+ =354 (calc. mol. wt.=354.4)

EXAMPLE 13

From methyl 4-(3-pyridyloxy)-3-N-pyrrolidinobenzoate and guanidine (procedure A). Melting point: >250° C.; MS: M+ =325 (calc. mol. wt.=325.36)

EXAMPLE 14

4-Chloro-3-N-piperidinobenzoylguanidine hydrochloride

From methyl 4-chloro-3-N-piperidinobenzoate and guanidine (procedure A). Melting point: 210°–212° C.; MS: M+ =280 (calc. mol. wt.=280.76)

EXAMPLE 15

4-Methyl-3-N-piperidinobenzoylguanidine hydrochloride

From methyl 4-methyl-3-N-piperidinobenzoate and guanidine (procedure A). Melting point: 160°–162° C.; MS: M+ =260 (calc. mol. wt.=260.33)

EXAMPLE 16

4-Chloro-3-N-pentylaminobenzoylguanidine hydrochloride

From methyl 4-chloro-3-N-pentylaminobenzoate and guanidine (procedure A). Melting point:80°–82° C.; MS: M+ =282 (calc. mol. wt.=282.77)

EXAMPLE 17

4-Dimethylaminobenzoylguanidine hydrochloride

From 4-dimethylaminobenzoic acid and guanidine (procedure B), colorless crystals, m.p.>285° C.

EXAMPLE 18

4-Piperidinobenzoylguanidine hydrochloride

From 4-piperidinobenzoic acid and guanidine (procedure B), colorless crystals, m.p. 189° C.,

EXAMPLE 19

3-Chloro-4-piperidinobenzoylguanidine hydrochloride

From 3-chloro-4-piperidinobenzoic acid and guanidine (procedure B), colorless crystals, m.p. 155° C.,

EXAMPLE 20

4-N-Methyl-N-(2-phenylethyl)aminobenzoylguanidine acetate

From 4-N-methyl-N-(2-phenylethyl)aminobenzoic acid and guanidine (procedure B), colorless crystals, m.p. 173° C.

Pharmacological Data

Anaesthetized rat with a coronary ligature a) Method

Male Sprague Dawley rats were anaesthetized with thiopental sodium in a dose of 100 mg/kg i.p. After opening and spreading of the pleural cavity, an access to the left coronary artery was created and a silk strip was incorporated around the left coronary artery by means of an atraumatic needle. After an equilibration period of 10 min, the substance was administered i.v. and 5 min later the coronary artery was occluded by means of the silk strip. Ventricular extrasystoles, ventricular tachyarrhythmias and ventricular fibrillation were determined according to the guidelines of the Lambeth convention (London, 1987). The substances were administered in DMSO/saline solution, such a solution containing 1 percent by volume of DMSO. In control experiments, the animals were treated with the solvent alone. The volume of solvent administered was 1 ml/kg in all cases.

b) Results:

The substance from Example 8 was administered in a dose of 1 mg/kg:

Duration of ventricular tachyarrhythmias: 4±2 sec (n=6) The following result was obtained with untreated control animals: 41±19 sec (n=4)

We claim:

1. A benzoylguanidine of the formula I

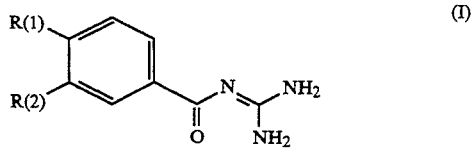

in which:

one of the two substituents R(1) or R(2) is —NR(3)R(4), where R(3) and R(4) together form a methylene chain $(CH_2)_n$, in which n is 4 or 5; and the other substituent R(1) or R(2) is chlorine, $C_1$-$C_4$-alkyl, $C_1$-$C_4$-alkoxy, or phenoxy, in which the phenyl radical is unsubstituted or substituted by one or two substituents selected from the group consisting of methyl, methoxy, fluorine or chlorine;

or its pharmaceutically tolerable salts.

2. A benzoylguanidine of the formula I as claimed in claim 1, in which the other substituent R(1) or R(2) is chlorine, $C_1$-$C_4$-alkoxy, or phenoxy, in which the phenyl radical is unsubstituted or substituted by one or two substituents selected from the group consisting of methyl, methoxy, fluorine or chlorine.

3. A benzoylguanidine of the formula I as claimed in claim 1, in which the other substituent R(1) or R(2) is chlorine or phenoxy, in which the phenyl radical is unsubstituted or substituted by one or two substituents selected from the group consisting of methyl, methoxy, fluorine or chlorine.

4. A benzoylguanidine of the formula I as claimed in claim 1, which is:
4-chloro-3-(1-pyrrolidino)benzoylguanidine, 4-methyl-3-(1-pyrrolidino)benzoylguanidine, 4-chloro-3-(1-piperidino)benzoylguanidine, 4-methyl-3-(1-piperidino)benzoylguanidine, 4-phenoxy-3-(1-pyrrolidino)benzoylguanidine and 4-(2-chlorophenoxy)-3-(1-pyrrolidino)benzoylguanidine or a pharmacologically tolerable salt thereof.

5. A method of treating arrhythmias comprising administering an effective amount for treating arrhythmias of a benzoylguanidine of formula I or its pharmaceutically tolerable salts as claimed in claim 1.

6. A method of prophylaxis or treatment of infarct in a mammal comprising administering an antiarrhythmic effective amount of a benzoylguanidine of formula I or its pharmaceutically tolerable salts as claimed in claim 1.

7. A method of treating angina pectoris in a mammal comprising administering an antiarrhythmic effective amount of a benzoylguanidine of formula I or its pharmaceutically tolerable salts as claimed in claim 1.

* * * * *